United States Patent
Slusar

(10) Patent No.: US 9,996,990 B2
(45) Date of Patent: Jun. 12, 2018

(54) ENHANCED VEHICLE BAD FUEL SENSOR WITH CROWDSOURCING ANALYTICS

(71) Applicant: Allstate Insurance Company, Northbrook, IL (US)

(72) Inventor: Mark Slusar, Chicago, IL (US)

(73) Assignee: Allstate Insurance Company, Northbrook, IL (US)

( * ) Notice: Subject to any disclaimer, the term of this patent is extended or adjusted under 35 U.S.C. 154(b) by 52 days.

(21) Appl. No.: 15/332,675

(22) Filed: Oct. 24, 2016

(65) Prior Publication Data

US 2018/0114378 A1    Apr. 26, 2018

(51) Int. Cl.
| | |
|---|---|
| G07C 5/08 | (2006.01) |
| G07C 5/00 | (2006.01) |
| G06Q 40/08 | (2012.01) |
| G01N 33/22 | (2006.01) |

(52) U.S. Cl.
CPC .......... *G07C 5/0808* (2013.01); *G06Q 40/08* (2013.01); *G07C 5/008* (2013.01); *G07C 5/0841* (2013.01); *G01N 33/22* (2013.01)

(58) Field of Classification Search
CPC .... G07C 5/0808; G07C 5/008; G07C 5/0841; G06Q 40/08; G01N 33/22
USPC ........................................................ 701/31.5
See application file for complete search history.

(56) References Cited

U.S. PATENT DOCUMENTS

| | | |
|---|---|---|
| 5,797,134 A | 8/1998 | McMillan et al. |
| 5,917,433 A | 6/1999 | Keillor et al. |
| 2003/0195676 A1 | 10/2003 | Kelly et al. |
| 2003/0216889 A1* | 11/2003 | Marko .................... G07C 5/008 702/182 |
| 2010/0030582 A1 | 2/2010 | Rippel et al. |
| 2012/0046982 A1 | 2/2012 | Wellman |
| 2012/0053759 A1 | 3/2012 | Lowrey et al. |
| 2014/0277902 A1 | 9/2014 | Koch |
| 2014/0379523 A1* | 12/2014 | Park ................... G06Q 30/0609 705/26.35 |
| 2015/0151682 A1 | 6/2015 | Gadotti |
| 2015/0179000 A1* | 6/2015 | Jayanthi ................. G01C 21/26 701/32.4 |

FOREIGN PATENT DOCUMENTS

WO    2016135532 A1    9/2016

OTHER PUBLICATIONS

Mechanic in a Bottle 2-In-I Gasoline Test Swab B3C Fuel Solutions, http://b3cfuel.com/products/mechanic-in-a-bottle-2-in-1-gasoline-test-swab, retrieved Mar. 23, 2016, 2 pages.

(Continued)

*Primary Examiner* — Brian P Sweeney
(74) *Attorney, Agent, or Firm* — Banner & Witcoff, Ltd.

(57) ABSTRACT

A fuel analysis system is described configured to assist vehicle drivers/users in preventing damage to their vehicles caused by bad fuel. Bad fuel can leave a driver and passengers stranded on the road in need of emergency road side service, and in many instances, results in permanent damage to the vehicle. The disclosed fuel analysis system describes an enhanced bad fuel sensor system that measures a delta in vehicle operation data to identify and in many instances, pre-emptively alert, a user of a vehicle of bad fuel. The fuel analysis system may use crowdsourcing through aggregation of refueling event profile records from a plurality of vehicles' telematics devices to increase the accuracy with which bad fuel is detected.

20 Claims, 9 Drawing Sheets

(56) References Cited

OTHER PUBLICATIONS

Got a Tank of Bad Gasoline? Texas Inspectors Will Check it Out, Deanna Dewberry, et al., 5NBCFW.com, http://www.nebcdfw.com/news/local/Got-A-Tank-of-Bad-Gasoline-Texas-Inspectors-Will-Check-it-Out-339573461.html, retrieved Mar. 23, 2016, 3 pages.
Bad Fuel: Fact or Fiction? Know Your Parts, http://www.knowyourparts.com/technical-articles/bad-fuel-fact-or-fiction, retrieved Mar. 23, 2016, 6 pages.
bad fuel & ruined engines—How?, Car Talk community page from May 2008, © 2016 Tappet Brothers LLC, 2 pages.
Bad diesel fuel Again . . . any suggestions?, Team Talk > Off Topic > off Topic Discussion, community pages from Jan. 23, 2012 through Apr. 26, 2012, 11 pages.
Diagnostics on the Move: Telematics Help Fleets Stay Ahead in Maintenance, Jim Beach, Nov. 2012, Truckinginfo.com, http://www.truckinginfo.com/article/story/2012/11/diagnositcs-on-the-move-telematics-help-fleets-stay-ahead-in-maintenance.aspx, retrieved Oct. 16, 2015, © 2015 Trucking Info, 5 pages.
Telematics Sensor-Equipped Trucks Help UPS Control Costs, Jul. 2010, by Shelley Mika, http://www.automotive-fleet.com/article/story/2010/07/green-fleet-telematics-sensor-equipped-trucks-help-ups-control-costs/page/2.aspx, retrieved Oct. 16, 2015, 5 pages.
What You Can Do to Avoid & Treat Bad Fuel, Apr. 14, 2015, http;//blog.briggsandstratton.com/stale-gasoline-can-avoid-treat-bad-fuel/, retrieved Mar. 23, 2016, 5 pages.
Texas Department of Agriculture, Fuel Stations Out of Compliance Report Jan. 21, 2016 to Mar. 21, 2016, https://texasagriculture.gov/Portals/0/Reports/PRI/stations_out_of order.html, retrieved Mar. 23, 2016, 12 pages.
Jan. 8, 2018—(WO) International Search Report—PCT/US17/57955.

* cited by examiner

ENHANCED VEHICLE BAD FUEL SENSOR WITH CROWDSOURCING ANALYTICS

TECHNICAL FIELD

Aspects of the disclosure generally relate to an improved sensor system in a vehicle relating to the measurement of fuel and fuel performance. In particular, various aspects of the disclosure involve a system integrated with an enhanced sensor system to improve the accuracy and/or timelines of bad fuel alerts.

BACKGROUND

A vehicle operates by consuming fuel, such as gasoline, diesel, or electricity in the case of electric/hybrid vehicles. Bad fuel can leave a driver and passengers stranded on the road in need of emergency road side service, and in many instances, results in permanent damage to the vehicle.

Meanwhile, vehicle telematics devices are known. Telematics includes the use of technology to communicate information from one location to another. Telematics has been used for various applications, including for the exchange of information with electronic sensors. As telematics technology has progressed, various communication methodologies have been incorporated into automobiles and other types of vehicles. Telematics systems such as on-board diagnostics (OBD) systems may be used in automobiles and other vehicles. OBD systems provide information from the vehicle's on-board computers and sensors, allowing users to monitor a wide variety of information relating to the vehicle systems, such as engine RPM, emissions control, coolant temperature, vehicle speed, timing advance, throttle position, and oxygen sensing, and many other types of data. Telematics devices installed within vehicles may be configured to access the vehicle computers and sensor data, and transmit the data to a display within the vehicle, a personal computer or mobile device, or to a centralized data processing system. Data obtained from OBD systems may be used for a variety of purposes.

While the risks and dangers of bad fuel have been known for a long time, there remains much room for improvement in the ability to detect bad fuel and to take actions to prevent the effects of the bad fuel from becoming epidemic.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

In one example, disclosed herein is an enhanced sensor system to detect bad fuel in a user vehicle. The system may comprise a user vehicle equipped with sensors configured to repeatedly measure a plurality of vehicle operation data indicative of bad fuel, a telematics device coupled to the user vehicle, and/or a server machine in wireless, remote communication with the telematics device. The sensors of the user vehicle may include, but are not limited to, an odometer, a clock, a fuel level gauge, and/or other circuitry. The user vehicle's sensors may repeatedly measure at least at a pre-refueling time that is before a refueling event and at a post-refueling time that is after the refueling event. Meanwhile, the telematics device may comprise one or more of: an electronic interface to the sensors of the user vehicle, a wireless communication circuitry, a user interface configured to communicate an alert to a user of the user vehicle, a processor configured to calculate a probability of having received bad fuel at the refueling event, and/or a computer memory.

In some examples, the processor of the telematics device may be programmed to perform steps comprising: detecting a refueling event upon receiving a substantial increase in a measurement of a fuel level gauge sensor of the user vehicle; receiving, through the electronic interface of the telematics device, the vehicle operation data measured by the sensors of the user vehicle at a pre-refueling time that is before the refueling event and at a post-refueling time that is after the refueling event; after detecting the refueling event, storing, in the computer memory of the telematics device, a refueling event profile record; comparing the vehicle operation data of the refueling event profile with vehicle operation data measured at the post-refueling time; determining that the two sets of vehicle operation data are different such that the probability of having received bad fuel at the refueling event is greater than zero; calculating a first confidence score for the probability of bad fuel based on a delta in the distance measurements and a delta in the time measurements during the comparing step; sending, through the wireless communication circuitry, the first confidence score to the server machine; and/or upon receipt of an updated first confidence score at the telematics device, causing the user interface of the telematics device to communicate an alert to the user of the user vehicle.

The refueling event profile record may comprise field including, but not limited to: a last set of the vehicle operation data measured by the sensors before the refueling event; a measurement of the fuel level gauge upon completion of the refueling event; a distance measurement, by an odometer sensor of the user vehicle, at the refueling event; a time measurement, by a clock of the user vehicle, at the refueling event; and a location measurement, by a global positioning satellite (GPS) unit, at the time of the refueling event.

In addition, the server machine may comprise one or more of: a vehicle operation database configured to store the plurality of vehicle operation data measured by the sensors, and a fuel analysis module, which is communicatively coupled to the vehicle operation database, configured to improve an accuracy of the probability of bad fuel. The fuel analysis module may be configured to perform one or more of the following steps: receive the first confidence score; update the first confidence score into a second confidence score based on those confidence scores provided by other vehicles associated with refueling event profile records that store a similar location measurement and similar time measurement as the refueling event profile record of the user vehicle; and/or send the second confidence score to the telematics device.

Aspects of the disclosure relate to methods, computer-readable media, and apparatuses for performing the method steps disclosed herein. Other features and advantages of the disclosure will be apparent from the additional description provided herein.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein.

DETAILED DESCRIPTION

In the following description of the various embodiments, reference is made to the accompanying drawings, which form a part hereof, and in which is shown by way of illustration, various embodiments of the disclosure that may be practiced. It is to be understood that other embodiments may be utilized.

Aspects of the disclosure illustrate a technological enhanced sensor system that enables the alerting and prediction of bad vehicle fuel. The technological improvements described herein permit more accurate detection of bad fuel by improving the accuracy of inputs received from numerous traditional sensors by implementing crowdsourcing functionality and through the synergy achieved by coupling the readings from multiple sensors and components, as described herein. Moreover, rather than simply considering absolute readings, in some examples, the enhance sensor system compares the change in sensor readings from before and after an event (e.g., a refueling event) to more accurately identify anomalies caused by the event. While technologies such as the Internet, wireless network communications, vehicle sensors, smartphone sensors, vehicle telematics, and vehicle on-board diagnostics (OBD), existed prior to Applicants' system embodied in the disclosure and claims, no single, technological system existed to enable a real-time pre-emptive alerting, maintenance, and/or prediction of bad fuel in a vehicle. The novel and non-obvious system disclosed herein is more than a general-purpose computer performing mundane, fundamental computer operations. Rather, the disclosed system, when viewed as a whole with the totality of its parts/components, provides advancement in a technical field because it, inter alia, results in a more accurate detection of bad fuel in a vehicle. While previous sensors may have existed for measuring the composition of fuel, such sensors failed to provide the higher level of accuracy provided by the novel and non-obvious fuel detection system described herein.

Figure 2A:
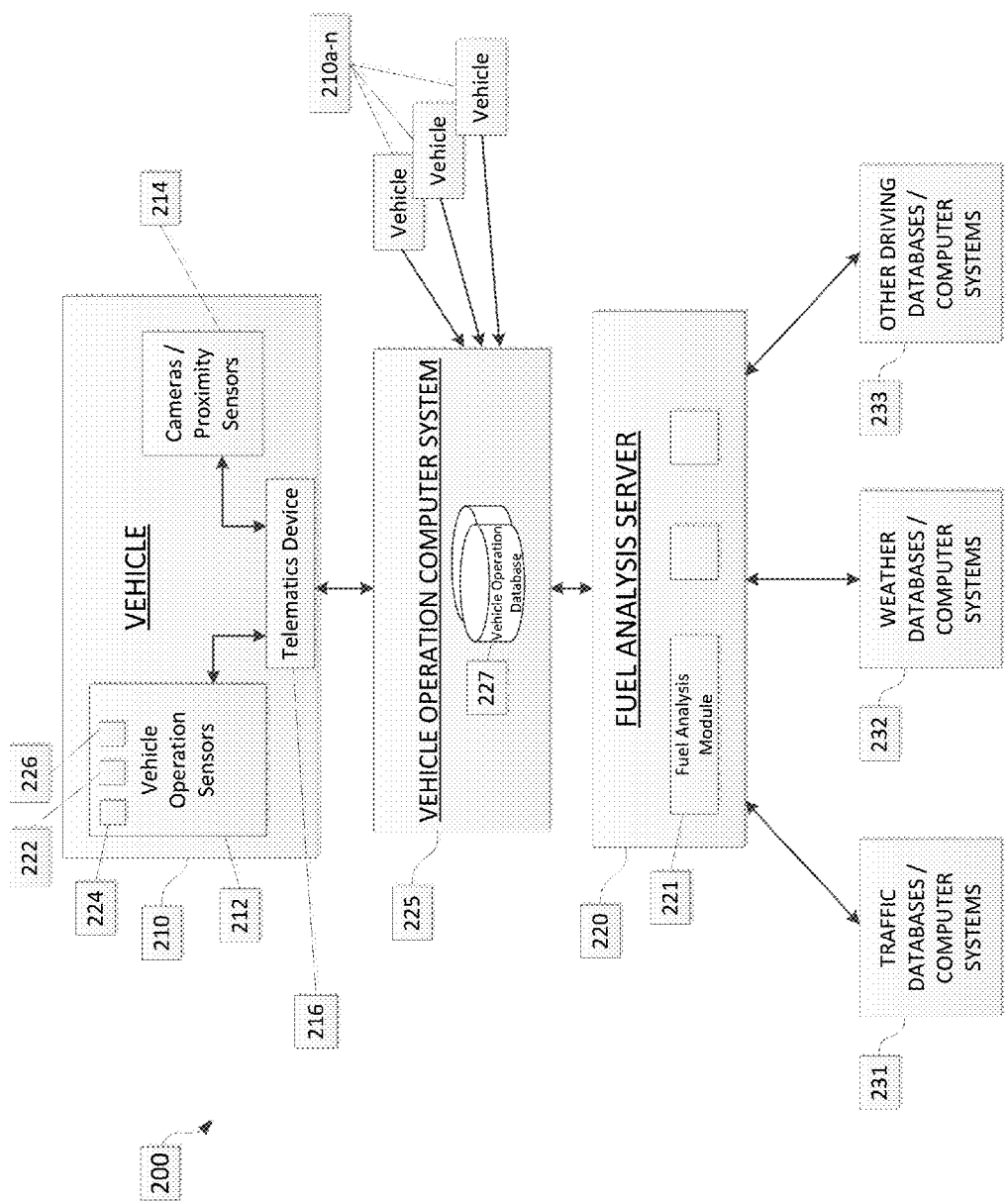
FIG. 2A and FIG. 2B are diagrams of fuel analysis systems, according to one or more aspects of the disclosure.

In some aspects of the disclosure, an enhanced bad fuel sensor (or sensor system) is described in which synergy is achieved through the collection and coordination of measurements from different components/apparatuses. In the illustrative system in FIG. 2A, the measurements from a GPS 224 component, odometer 222, and/or timer/clock component 226 may be coupled with those of vehicle operation measurements to more accurately detect and generate alerts for bad fuel of a vehicle. Moreover, the system in FIG. 2A is coupled to a network (e.g., the Internet or a wireless network) to aggregate coupled measurements to increase the statistical accuracy of prediction and detection of bad fuel of a vehicle. While the system described herein relies upon processors 103, memory 115, and the receipt and transmission of data over one or more networks 131, the totality of the system described herein previously never existed to aggregate and improve the accuracy of detection and prediction of bad fuel of a vehicle.

Figure 1:
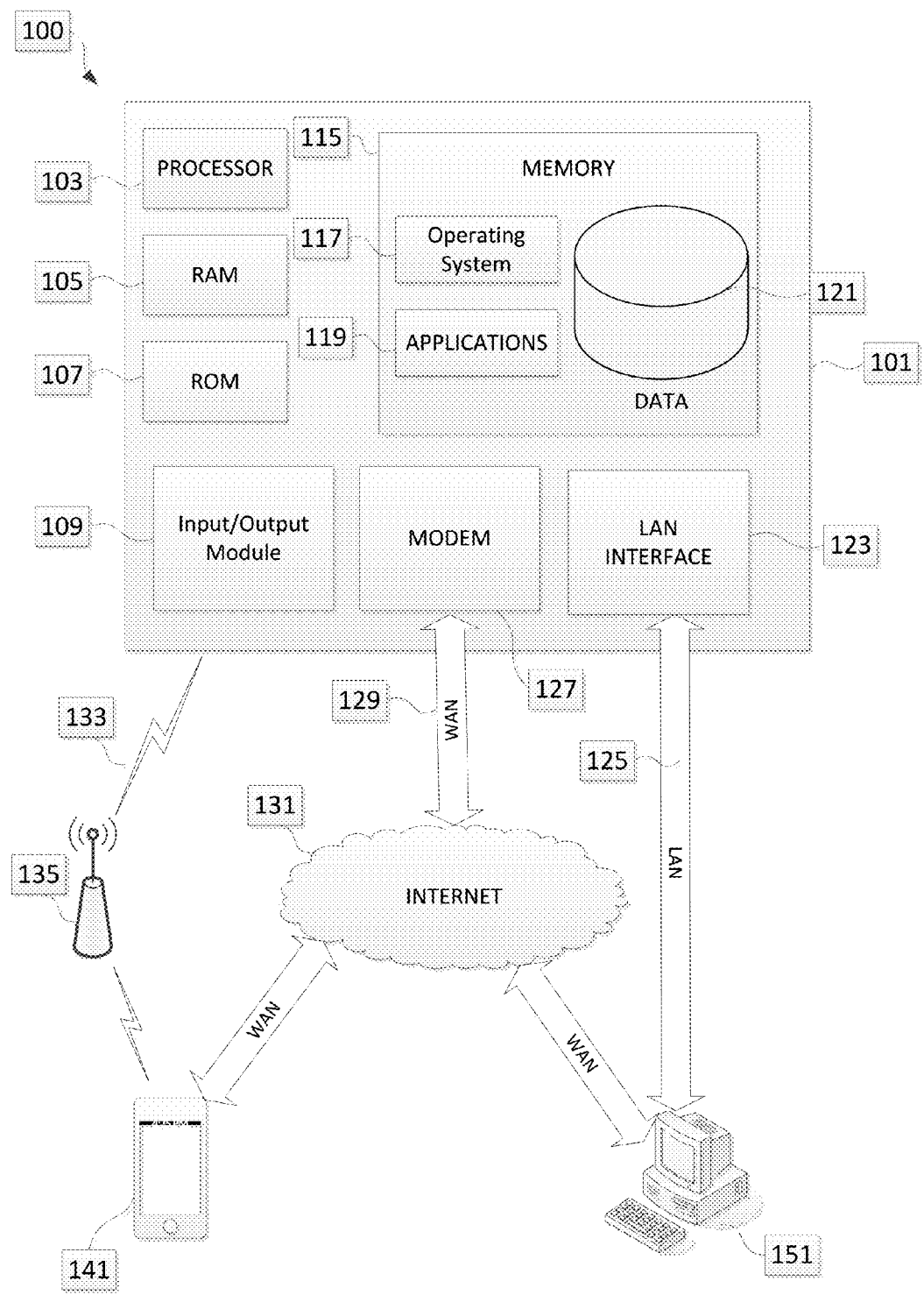
FIG. 1 illustrates a network environment and computing systems that may be used to implement aspects of the disclosure.

FIG. 1 illustrates a block diagram of a computing device (or system) 101 in communication system 100 that may be used according to one or more illustrative embodiments of the disclosure. The device 101 may have a processor 103 for controlling overall operation of the device 101 and its associated components, including RAM 105, ROM 107, input/output module 109, and memory 115. The computing device 101, along with one or more additional devices (e.g., terminals 141, 151) may correspond to any of multiple systems or devices, such as a fuel analysis server or system, configured as described herein for receiving and analyzing vehicle operation data and calculating bad fuel scores based on fuel analysis.

Input/Output (I/O) 109 may include a microphone, keypad, touch screen, and/or stylus through which a user of the computing device 101 may provide input, and may also include one or more of a speaker for providing audio output and a video display device for providing textual, audiovisual and/or graphical output. Software may be stored within memory 115 and/or storage to provide instructions to processor 103 for enabling device 101 to perform various functions. For example, memory 115 may store software used by the device 101, such as an operating system 117, application programs 119, and an associated internal database 121. Processor 103 and its associated components may allow the fuel analysis system 101 to execute a series of computer-readable instructions to receive a vehicle operation data from a first vehicle, retrieve additional vehicle operation data for other vehicles corresponding to first vehicle operation data, and perform fuel analysis of the first vehicle.

In some embodiments, the fuel analysis system 101 may operate in a networked environment 100 supporting connections to one or more remote computers, such as terminals 141 and 151. The terminals 141 and 151 may be personal computers, servers (e.g., web servers, database servers), or mobile communication devices (e.g., vehicle telematics devices, on-board vehicle computers, mobile phones, portable computing devices, and the like), and may include some or all of the elements described above with respect to the fuel analysis system 101. The network connections depicted in FIG. 1 include a local area network (LAN) 125 and a wide area network (WAN) 129, and a wireless telecommunications network 133, but may also include other networks. When used in a LAN networking environment, the fuel analysis system 101 may be connected to the LAN 125 through a network interface or adapter 123. When used in a WAN networking environment, the system 101 may include a modem 127 or other means for establishing communications over the WAN 129, such as network 131 (e.g., the Internet). When used in a wireless telecommunications network 133, the system 101 may include one or more transceivers, digital signal processors, and additional circuitry and software for communicating with wireless computing devices 141 (e.g., mobile phones, vehicle telematics devices) via one or more network devices 135 (e.g., base transceiver stations) in the wireless network 133.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, and WiMAX, is presumed, and the various computing devices and fuel analysis system components described herein may be configured to communicate using any of these network protocols or technologies.

Additionally, one or more application programs 119 used by the fuel analysis server/system 101 may include computer executable instructions (e.g., fuel analysis programs and bad fuel score algorithms) for receiving vehicle operation data, retrieving additional operation data for other vehicles, analyzing and comparing the vehicle operation data with respect to specific vehicle operation behaviors, performing a fuel analysis or computation for one or more vehicles or drivers, and performing other related functions as described herein.

Figure 2B:
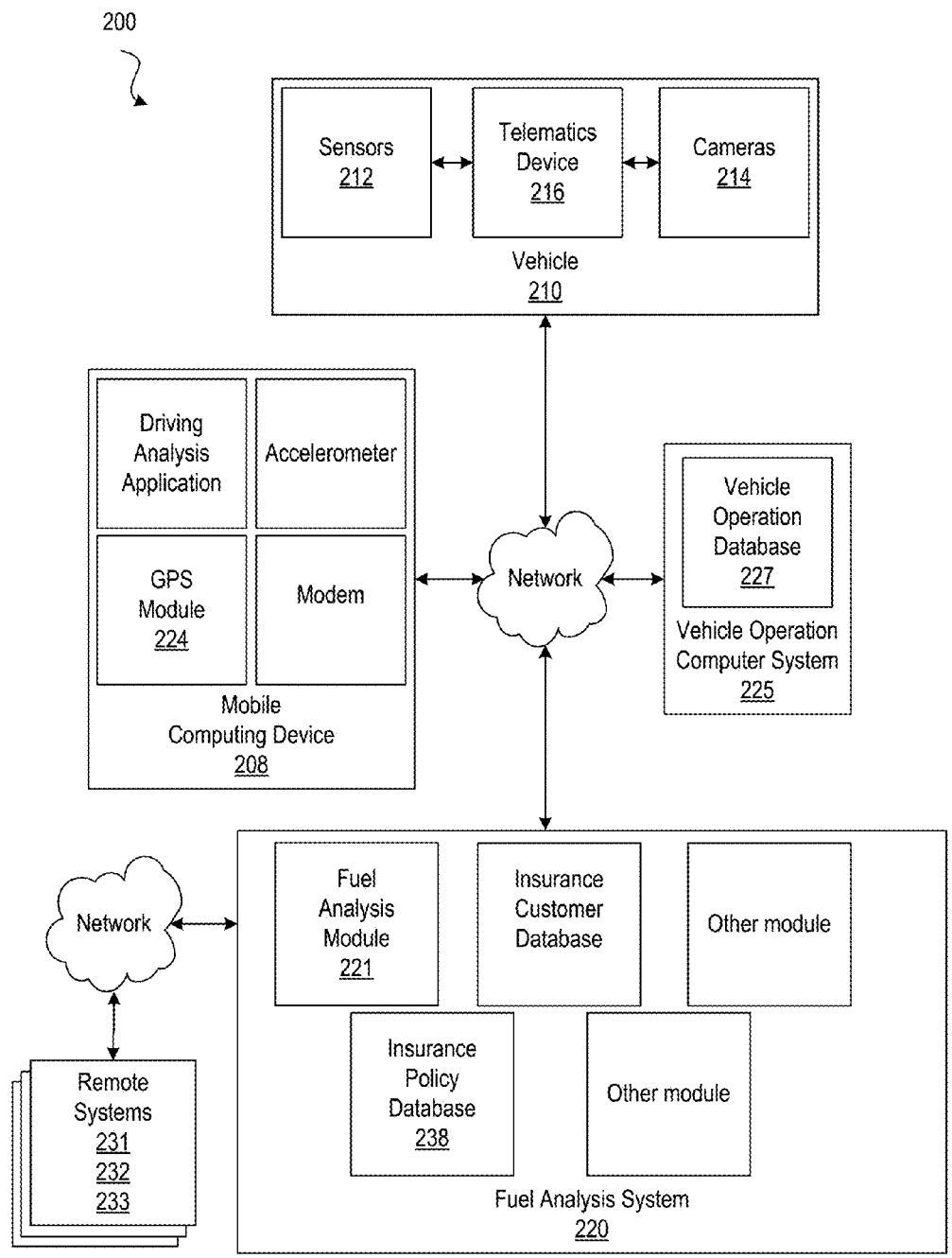

FIG. 2A and FIG. 2B (collectively "FIG. 2") are diagrams of an illustrative fuel analysis system 200. Each component shown in FIG. 2 may be implemented in hardware, software, or a combination of the two. Additionally, each component of the fuel analysis system 200 may include a computing device (or system) having some or all of the structural components described above for computing device 101.

The fuel analysis system 200 shown in FIG. 2 includes a vehicle 210, such as an automobile, motorcycle, or other vehicle for which a fuel analysis may be performed and for which bad fuel may be detected, predicted, and/or an alert generated. The vehicle 210 may include one or more on-board data recording systems, for example, on-board diagnostic (ODB) systems, telematics devices 216, and/or vehicle computer systems, which may include or may be configured to communicate with vehicle sensors 212, proximity sensors and cameras 214, and other on-board data detection devices.

In some examples, the fuel analysis system 200 may analyze vehicle operation data and calculate bad fuel scores. As used herein, a bad fuel score may refer to a measurement of a probability that the fuel currently in the vehicle's 210 is tainted in some way with impurities. The bad fuel score may be a numeric value, a preset range of values (e.g., high, medium, low), color-based indicators (e.g., red, orange, green), or any other indication that conveys information to a user. Unlike bad fuel detection sensors that may (or may not) already exist, the technological improvements described herein permit more accurate detection of bad fuel. For example, the fuel analysis system 200 operates by receiving inputs from numerous traditional sensors, and enhancing their accuracy by implementing crowdsourcing functionality and/or through the synergy achieved by coupling the readings from multiple sensors and components, as described herein, and analyzing pre- and post-refueling readings.

With reference to FIG. 2, vehicle operation sensors 212 refer to a set of sensors and data detection devices capable of detecting and recording various conditions at the vehicle and operational parameters of the vehicle. For example, sensors 212 may detect and store data corresponding to the vehicle's speed, distances driven, rates of acceleration or braking, and specific instances of sudden acceleration, braking, and swerving. Sensors 212 also may detect and store data received from the vehicle's 210 internal systems, such as impact to the body of the vehicle, air bag deployment, headlights usage, brake light operation, door opening and closing, door locking and unlocking, cruise control usage, hazard lights usage, windshield wiper usage, horn usage, turn signal usage, seat belt usage, phone and radio usage within the vehicle, maintenance performed on the vehicle, and other data collected by the vehicle's computer systems. Additional sensors 212 may detect and store the external driving conditions, for example, external temperature, rain, snow, light levels, and sun position for driver visibility. Sensors 212 also may detect and store data relating to moving violations and the observance of traffic signals and signs by the vehicle 210. Additional sensors 212 may detect and store data relating to the maintenance of the vehicle 210, such as the engine status, oil level, engine coolant temperature, odometer reading, the level of fuel in the fuel tank, engine revolutions per minute (RPMs), and/or tire pressure. The vehicle 210 also may include one or more cameras and proximity sensors 214 capable of recording additional conditions inside or outside of the vehicle 210. Internal cameras 214 may detect conditions such as the number of the passengers in the vehicle 210, and potential sources of driver distraction within the vehicle (e.g., pets, phone usage, unsecured objects in the vehicle). External cameras and proximity sensors 214 may detect other nearby vehicles, traffic levels, road conditions, traffic obstructions, animals, cyclists, pedestrians, and other conditions that may factor into a fuel analysis.

The operational sensors 212 and the cameras and proximity sensors 214 may store data within the vehicle 210, and/or may transmit the data to one or more external computer systems (e.g., a vehicle operation computer system 225 and/or a fuel analysis server 220). As shown in FIG. 2, the operation sensors 212, and the cameras and proximity sensors 214, may be configured to transmit data to a vehicle operation computer system 225 via a telematics device 216. In other examples, one or more of the operation sensors 212 and/or the cameras and proximity sensors 214 may be configured to transmit data directly without using a telematics device 216. For example, telematics device 216 may be configured to receive and transmit data from operational sensors 212, while one or more cameras and proximity sensors 214 may be configured to directly transmit data to a vehicle operation computer system 225 or a fuel analysis server 220 without using the telematics device 216. Thus, telematics device 216 may be optional in certain embodiments where one or more sensors or cameras 212 and 214 within the vehicle 210 may be configured to independently capture, store, and transmit vehicle operation and fuel data.

Telematics device 216 may be a computing device containing many or all of the hardware/software components as the computing device 101 depicted in FIG. 1. As discussed above, the telematics device 216 may receive vehicle operation and vehicle operation data from vehicle sensors 212, and proximity sensors and cameras 214, and may transmit the data to one or more external computer systems (e.g., a vehicle operation computer system 225 and/or a fuel analysis server 220) over a wireless transmission network. Telematics device 216 also may be configured to detect or determine additional types of data relating to real-time driving and the condition of the vehicle 210. In certain embodiments, the telematics device 216 may contain or may be integral with one or more of the vehicle sensors 212 and proximity sensors and cameras 214 discussed above, and/or with one or more additional sensors discussed below.

Additionally, in some examples, the telematics device 216 may be configured to collect data regarding the number of passengers and the types of passengers (e.g. adults, children, teenagers, pets, etc.) in the vehicle 210. The telematics device 216 also may be configured to collect data a driver's movements or the condition of a driver. For example, the telematics device 216 may include or communicate with sensors that monitor a driver's movements, such as the driver's eye position and/or head position, etc. Additionally, the telematics device 216 may collect data regarding the physical or mental state of the driver, such as fatigue or intoxication. The condition of the driver may be determined through the movements of the driver or through sensors, for example, sensors that detect the content of alcohol in the air or blood alcohol content of the driver, such as a breathalyzer.

The telematics device 216 also may collect information regarding the driver's route choice, whether the driver follows a given route, and to classify the type of trip (e.g. commute, errand, new route, etc.). In certain embodiments, the telematics device 216 may be configured to communicate with the sensors and/or cameras 212 and 214 to determine when and how often the vehicle 210 stays in a single lane or strays into other lanes. To determine the vehicle's route, lane position, and other data, the telematics device 216 may include or may receive data from a mobile telephone, a Global Positioning System (GPS) unit 224, locational sensors positioned inside a vehicle, or locational sensors or devices remote from the vehicle 210.

The telematics device 216 also may store the type of the vehicle 210, for example, the make, model, trim (or sub-model), year, and/or engine specifications. The vehicle type may be programmed into the telematics device 216 by a user or customer, determined by accessing a remote computer system, such as an insurance company or financial institution server, or may be determined from the vehicle itself (e.g., by accessing the vehicle's 210 computer systems).

Vehicle operation computer system 225 may be a computing device separate from the vehicle 210, containing some or all of the hardware/software components as the computing device 101 depicted in FIG. 1. The vehicle operation computer system 225 may be configured to receive and store the vehicle operation data discussed above from vehicle 210, and similar vehicle operation data from one or more other vehicles 210a-n. In the example shown in FIG. 2, the vehicle operation computer system 225 includes a vehicle operation database 227 that may be configured to store the vehicle operation data collected from the vehicle sensors 212, proximity sensors and cameras 214, and telematics devices 216 of a plurality of vehicles. The vehicle operation database 227 may store operational sensor data, proximity sensor data, camera data (e.g., image, audio, and/or video), location data and/or time data for multiple vehicles 210.

Figure 5:
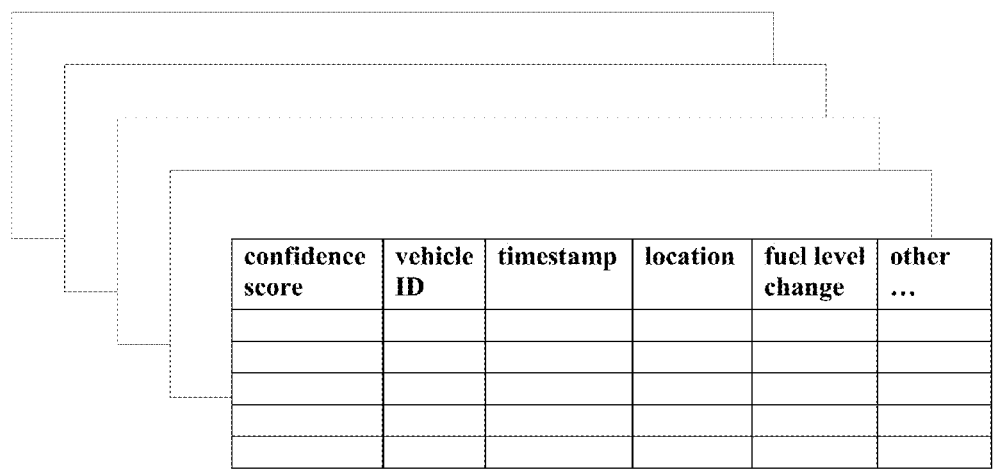
FIG. 5 illustrates a data structure optimized for storing and calculating the probability of bad fuel having been provided by a particular fuel provider, in accordance with one or more aspects of the disclosure.

Data stored in the vehicle operation database 227 may be organized in any of several different manners. For example, a table in the vehicle operation database 227 may contain all of the vehicle operation data for a specific vehicle 210, similar to a vehicle event log. Other tables in the vehicle operation database 227 may store certain types of data for multiple vehicles. Vehicle operation data may also be organized by time, so that the driving behaviors of multiples vehicles 210 may be stored or grouped by time (e.g., morning, afternoon, late night, rush hour, weekends, etc.) as well as location. Furthermore, other tables in the vehicle operation database 227 may be organized by refueling station location such that vehicles that have refueled at that location are included in an array (or linked list structure) by chronological order of their refueling event, as illustrated in FIG. 5 and described herein.

The system 200 also includes a fuel analysis server 220, containing some or all of the hardware/software components as the computing device 101 depicted in FIG. 1. The fuel analysis server 220 may include hardware, software, and network components to receive vehicle operation data from the vehicle operation computer system 225 and/or directly from a plurality of vehicles 210. The fuel analysis server 220 and the vehicle operation computer system 225 may be implemented as a single server/system, or may be separate servers/systems. In some examples, the fuel analysis server 220 may be a central server configured to receive vehicle operation data from a plurality of remotely located vehicle operation computer systems 225.

As shown in FIG. 2, fuel analysis server 220 may include a fuel analysis module 221 among other modules. The modules 221 may be implemented in hardware and/or software configured to perform a set of specific functions within the fuel analysis server 220. For example, the fuel analysis module 221 may include one or more fuel analysis score calculation algorithms, which may be executed by one or more software applications running on generic or specialized hardware within the fuel analysis server 220. The fuel analysis module 221 may use the vehicle operation data received from the vehicle operation computer system 225 and/or other systems to perform bad fuel analyses for specific vehicles 210. The module 221 may calculate or adjust a bad fuel confidence score for a vehicle 210 based on one or more factors. Further descriptions and examples of the algorithms, functions, and analyses that may be executed by the fuel analysis module 221 are described below in reference to FIG. 3A, FIG. 3B, FIG. 3C, and FIG. 3D.

To perform bad fuel analyses and calculations, the fuel analysis server 220 may initiate communication with and/or retrieve data from one or more vehicles 210, vehicle operation computer systems 225, and additional computer systems 231-233 storing data that may be relevant to the analysis and calculations. For example, one or more traffic data storage systems 231, such as traffic databases, may store data corresponding to the amount of traffic and certain traffic characteristics (e.g., amount of traffic, average driving speed, traffic speed distribution, and numbers and types of accidents, etc.) at various specific locations and times. One or more weather data storage systems 232, such as weather databases, may store weather data (e.g., rain, snow, sleet, hail, temperature, wind, road conditions, visibility, etc.) at different locations and different times. One or more additional driving databases/systems 233 may store additional driving data from one or more different data sources or providers which may be relevant to the bad fuel analyses and/or confidence score calculations performed by the fuel analysis server 220. Additional databases/systems 233 may store data regarding events such as road hazards and traffic accidents, downed trees, power outages, road construction zones, school zones, and natural disasters that may affect the analyses and/or score calculations performed by the fuel analysis server 220.

The various sensors and measurement devices described herein (e.g., vehicle operations sensors 212, proximity sensors 214, and others) may be coupled such that the readings from these devices are linked in a data structure in computer memory. In other words, the accuracy of a bad fuel sensor is enhanced through the collection and coordination of measurements from the different components/apparatuses illustrated in FIG. 2A. In one example (i.e., "setup" example), a myriad of measurements may be recorded in non-volatile memory when a fuel level gauge sensor detects a change in the fuel level. In another example (i.e., "crowd-sourcing" example), the enhanced bad fuel sensor system may query a fuel analysis server 220 to enhance the accuracy of a determination that a bad fuel sensor measurement is not a false positive. In yet another example (i.e., "garage" example), the enhanced bad fuel sensor system may consider the change (e.g., delta) in particular sensor measurements before and after a potential refueling event to adjust the enhanced bad fuel sensor system's confidence that bad fuel was added to the vehicle 210. Finally, in another example (i.e., "warning" example), a fuel analysis server 220 may generate a notification (e.g., an alert) to pre-emptively alert vehicles 210a-n that they may have been refueled with bad fuel, and others, such as fuel providers, insurance policy providers, roadside assistance service providers, and others.

Figure 3A:
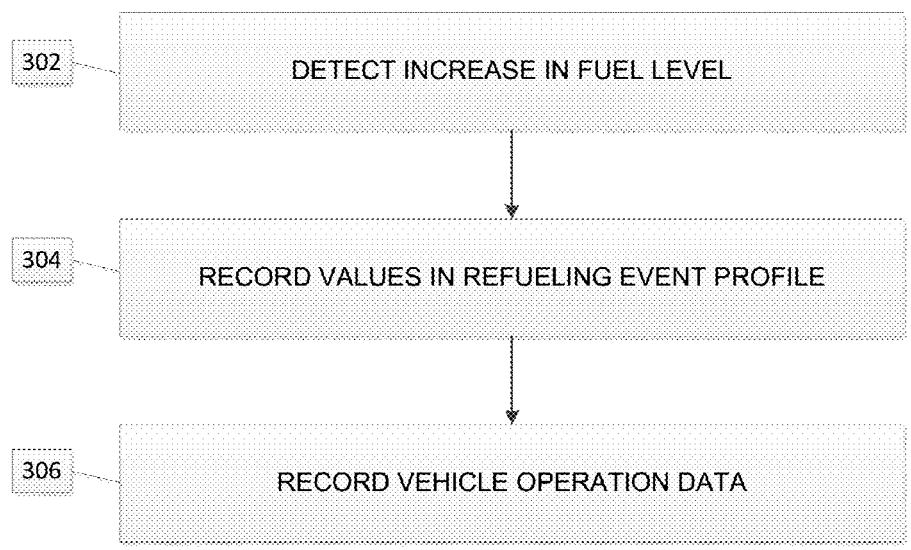
FIG. 3A, FIG. 3B, FIG. 3C, AND FIG. 3D are flow diagrams showing illustrative methods of enhancing the detection of bad fuel in accordance with one or more aspects of the disclosure.

As illustrated in FIG. 3A, in one version of the "setup" example, when the sensor 212 for measuring fuel level gauge reads a substantial increase in the fuel level in the vehicle 210, a telematics device 216 may cause the system 200 to record particular measurements. A substantial increase is a pre-programmed change in the fuel level of a vehicle that exceeds a minimum threshold value (e.g., more than a quarter tank full, more than 4 gallons of fuel, more than a one-half charge, or other thresholds) such that false refueling readings are avoided (e.g., from a vehicle driving up/down a hill, hitting a pothole, etc.). In an example where vehicle 210 is an electric vehicle (or a hybrid-electric vehicle), the vehicle may comprise an engine at least partially powered by an electric battery. In such examples, the fuel level gauge might not be a measure of a fuel tank level; rather, the fuel level gauge may be a measure of the remaining electric charge of the vehicle battery. In such situations, a substantial increase in the fuel level may amount to more than a ten percent (or other predetermined percentage or amount) increase in the battery's charge.

Referring to FIG. 3A, in step 302 the telematics device 216 may detect a substantial increase in the measured fuel level gauge since the last time the value was measured. As a result, the telematics device 216 may record in step 304 the current values of a plurality of sensors 212, 214 into non-volatile (e.g., persistent) computer memory, for example, as a refueling event profile record. The values recorded may include the new, updated fuel level gauge once the increase in the gauge level subsides. Moreover, a delta in the fuel level gauge since the last occurrence of a substantial increase (e.g., refueling event), may also be recorded in the record. In addition, the values measured and recorded may include a GPS sensor 224 reading at the time of the refueling event, an odometer 222 reading at the time of the refueling event, and/or a clock/timer 226 reading with the time/date at the time of the refueling event. One or more of the aforementioned values recorded in step 304 may be optional in some examples. For example, in vehicles where a GPS sensor 224 is absent, the telematics device 216 may attempt to engage in near-field-communication (NFC) with one or more wireless (e.g., BLUETOOTH™, WiFi, RFID) devices at the fuel provider's location; if successful, in one example, the vehicle's refueling database records may then be successfully linked to the unique identifier assigned to the fuel provider at that particular location. A person skilled in the art after review of the entirety disclosed herein will appreciate that GPS sensor 224 need not be limited to just GPS technology. Rather, GPS sensor 224 is contemplated to encompass any location detection device/component/system (e.g., triangulation, NFC, etc.) that is able to determine the location of the vehicle at the time of refueling.

In the "setup" example of FIG. 3A, the database records may be stored local to the vehicle 210. The storage may take place in persistent memory cells in the telematics device 216. In another example, the memory storage may be integrated in the vehicle 210. In either example, a telematics device 216 comprises wireless communication hardware to provide for communication with a remote computer system (e.g., vehicle operation computer system 225, fuel analysis server 220, etc.). In another example, the memory storage may extend from the local vehicle 210 to a remote server (e.g., system 225, or others).

The values recorded in step 304 may be linked with a unique identifier associated with the event (e.g., refueling event) corresponding to the fuel level gauge increasing. Linking may be accomplished, in one example, by including an identifier in each database record storing the recorded values. In another example, the database records may be stored in a linear (e.g., flat) format such that the processing time associated with a hierarchy database structure is ameliorated. In either example, the data values recorded in step 304 may represent a refueling event profile of the vehicle. The refueling event profile comprises information to assist in identifying the circumstances around which a vehicle 210 was refueled, such as the location where it was refueled, the date/time when it was refueled, the total number of miles the vehicle had been driven when it was refueled, and/or the amount of fuel that was added to the vehicle. The refueling event profile may be stored in computer memory and linked with other records as explained above.

Referring to FIG. 3A, in step 306 the telematics device 216 may collect vehicle operation data, such as those discussed above, about vehicle 210, including but not limited to data measured from the vehicle sensors 212, proximity sensors and cameras 214, telematics devices 216, and/or other external sensor systems. For example, the collected data may include operational sensor data, proximity sensor data, camera data (e.g., image, audio, and/or video), location data and/or time data for a vehicle 210. The vehicle operation data may be stored in a vehicle operation database 227 and organized in any of several different manners. As explained above, in one example, a table in the vehicle operation database 227 may contain all of the vehicle operation data for a specific vehicle 210, similar to a vehicle event log. Other tables in the vehicle operation database 227 may store certain types of data for multiple vehicles. For instance, some tables may store refueling event data for a particular fuel provider location such that the database 227 can efficiently link to appropriate vehicle operation data. Vehicle operation data may also be organized by time, so that the vehicle operation characteristics of multiples vehicles 210a-n may be stored or grouped by time (e.g., morning, afternoon, late night, rush hour, weekends, predetermined range of specific time, etc.) as well as where they experienced a refueling event.

For example, after experiencing a refueling event, a telematics device 216 may request a vehicle 210 to provide vehicle operation data. Alternatively, the telematics device 216 may have previously registered with the vehicle 210 to receive vehicle operation data, e.g., through the vehicle's on-board diagnostics (OBDII) port or other interface. In yet another example, the telematics device may obtain vehicle operation data from sources other than (or in addition to) the vehicle 210, such as from sensors (e.g., accelerometer, gyroscope, altimeter, barometer, thermometer, etc.) installed inside the telematics device 216 itself or external to the vehicle 210 (e.g., traffic cameras, wireless devices, weather databases 232, etc.).

In conjunction with the vehicle operation data, the telematics device 216 also obtains and records the amount of time that has elapsed between the current time and the time of the refueling event. For example, the telematics device may determine this value by calculating the difference in the timestamp value recorded in the refueling event profile with the current value indicated on the vehicle's 210 clock 226. Similarly, the telematics device also obtains and records the number of miles (or kilometers or other units of distance) that the vehicle 210 has been driven since the refueling event. For example, the telematics device 216 may determine this value by calculating the difference in the odometer value recorded in the refueling event profile with the current value of the vehicle's 210 odometer 222. Finally, in those vehicles (optionally) equipped with a bad fuel sensor, the output of the bad fuel sensor may also be included in the vehicle operation data being requested and/or recorded at this time. All of the aforementioned values may be referred to as vehicle operation data with respect to fuel analysis system 200.

This vehicle operation data may be collected, processed, and/or recorded in computer memory by the telematics device 216. The recording may occur at regular intervals of time, or alternatively at irregular (e.g., upon a triggering event, at random times, on-demand) intervals of time. For example, the telematics device 216 may record the first set of vehicle operation data at a predetermined amount of time (e.g., 3 minutes, 5 minutes, or other amount of time) or predetermined quantity of distance (e.g., 1 mile, 3 miles, or other quantity of distance) after occurrence of a refueling event. Assuming no bad fuel is positively detected, the telematics device 216 may automatically continue to track the vehicle operation data at regular, recurring intervals of time/distance (e.g., at each 5 minute interval, or each 3-mile interval) or at irregular intervals (e.g., at t=5 minutes, t=15 minutes, t=30 minutes, t=50 minutes, and so on until the next refueling event and/or the end of trip (EOT)).

To summarize, some input factors collected by the fuel analysis system 200 at one or more times after the occurrence of a refueling event include, but are not limited to, (1) the value read from a (optional) bad fuel sensor of the vehicle 210; (2) a delta in the values of those vehicle operation data variables that are indicative of bad fuel; (3) the delta in vehicle odometer 222 readings; and/or (4) the delta in clock 226 readings. The fuel analysis system 200 operates by monitoring one or more of at least the aforementioned four input factors to more accurately detect bad fuel in vehicles 210a-n. Moreover, in contrast to traditional sensor systems, in some examples the fuel analysis system 200 enhances the accuracy of the aforementioned input factors with an additional input factor: information from crowdsourcing functionality. Several additional, illustrative examples are described in turn below.

By way of overview, in one example (i.e., "garage" example), the enhanced bad fuel sensor system may consider the change (e.g., delta) in particular sensor measurements before and after a potential refueling event to adjust the enhanced bad fuel sensor system's confidence that bad fuel was added to the vehicle 210. The disclosure contemplates other examples of uses of the fuel analysis system 200 disclosed herein and should not be construed to be limited to just the examples expressly described herein.

In the "garage" example, an enhanced bad fuel sensor system 200 adjusts the confidence score corresponding to the probability that bad fuel was added to the vehicle 210 at its last refueling. The confidence score may be stored in computer memory local to the telematics device 216. Meanwhile, if the system 200 includes crowdsourcing functionality, then the confidence score will also be stored at a remote server system (e.g., system 225, server 220, etc.). For purposes of illustration, assume that in the "garage" example the vehicle 210 is refueled at a date and time (t=0) at GPS coordinates of X0 longitude, Y0 latitude as measured by the vehicle's location detection component (e.g., GPS 224) at the time of refueling. The telematics device 216 detects an increase in the fuel level from a ¼-full tank to a ¾-tank gauge level and triggers the creation of a new refueling event profile record in local computer memory 115. The refueling event profile (e.g., a database record) may store/record information identifying the circumstances around which the vehicle 210 was refueled, such as (1) the location where it was refueled, (2) the date/time when it was refueled, (3) the total number of miles the vehicle had been driven when it was refueled, and/or (4) the approx. quantity of fuel that was added to the vehicle. These values are recorded in computer memory by the telematics device 216.

Figure 3B:
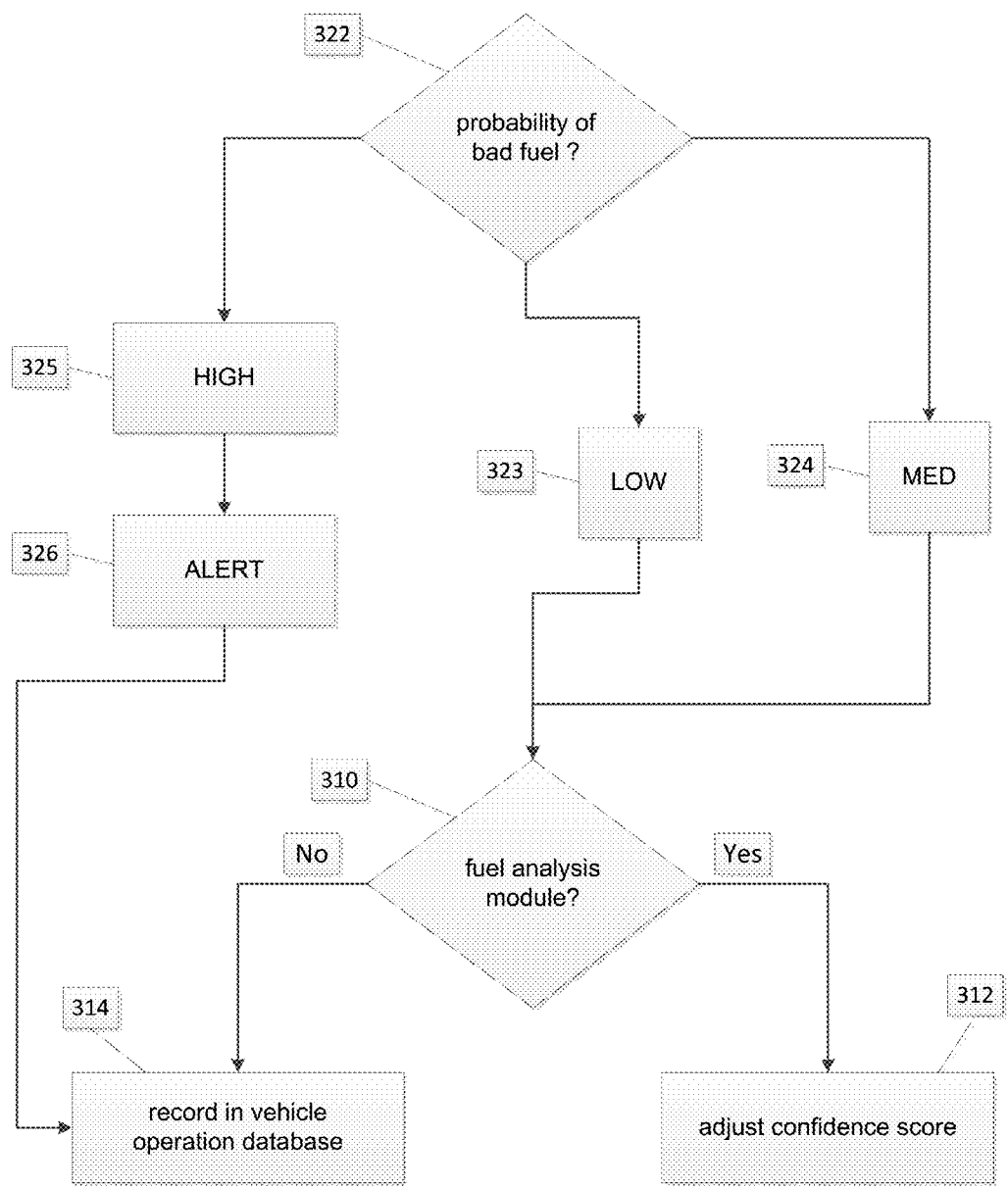
Figure 3C:
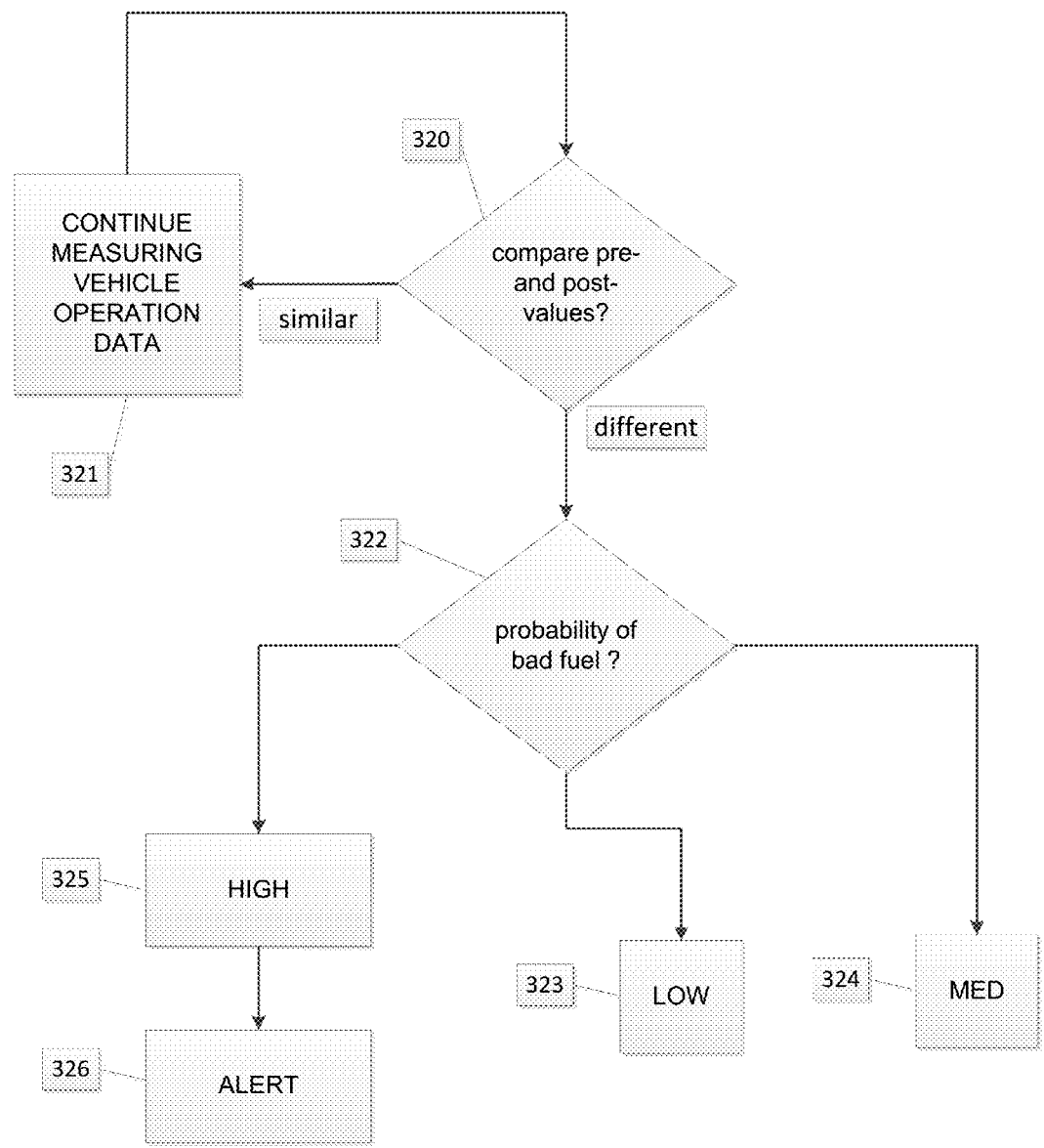

FIG. 3C is a flow diagram illustrating the "garage" example in which fuel analysis is performed based on vehicle operation data. Assume for the purposes of illustration, in the "garage" example the vehicle 210 is parked in a garage almost immediately after refueling. And as such, the end of trip (EOT) may occur within thirty seconds (i.e., t=30 seconds) after refueling. In such an example, the telematics device 216 might not have had an opportunity to collect statistically useful vehicle operation data after the refueling event in order to compare it to the pre-refueling vehicle operation data recorded in memory. Meanwhile, assume for purposes of this illustration that the vehicle 210 is not driven again for two days. As such, assume at time t=2,880 minutes (i.e., approx. two days later), the vehicle 210 is started and taken on a trip that last sixty minutes, and the vehicle is driven fifty total miles during that trip. At time t=2,885 minutes (i.e., about five minutes into the start of the trip), the telematics device 216 may retrieve the current vehicle operation data of the vehicle 210 and compare it, in step 320, to the last vehicle operation data recorded pre-refueling (i.e., at a time t<0).

In step 320, the processor 103 of the telematics device 216 may compare the pre-refueling recorded values (e.g., the ones from time t<0) to the newly acquired readings obtained post-refueling (e.g., the ones from t=2,885 minutes). In some examples, the aforementioned comparison may include using the output from a bad fuel sensor, which detects bad fuel, to predict the presence of bad fuel in a vehicle 210. Meanwhile, in some examples, one or more types of vehicle operation data may be used to predict the presence of bad fuel in a vehicle 210. For example, vehicle operation data such as, engine revolutions per minute (RPM), rate of fuel consumption, oxygen sensor readings, irregular starts/stops/stalling/knocking of engine cylinders, engine status, engine timing, engine temperature, vehicle exhaust/emission controls, oil level, and/or other types of vehicle operation data may be used to detect the presence of bad fuel in a vehicle 210. In yet another example, assuming the vehicle is an electric/hybrid vehicle, the vehicle operation data may include, but is not limited to, the voltage and/or amperage being received when the vehicle's battery is connected at a recharging station. Such vehicle operation data may assist in detecting a bad connection/connector when the battery is at the refuel station. In addition, the vehicle operation data may assist in detecting if the vehicle's battery is being charged too quickly or too slow such that it may be damaged. Some batteries may be incapable of handling a fast/super-fast charge that may be provided by some refuel/re-charge stations.

In particular, the telematics device 216 may receive readings for the aforementioned types of vehicle operation data. If the comparison (step 320) shows that the values remain the same, or even sufficiently similar, then the telematics device 216 may (in step 321) simply record the values in computer memory and generate no alert indicating bad fuel. After step 321, the telematics device 216 may await the occurrence of the next interval to again measure the vehicle operation data, as done in step 306 (referring to FIG. 3A).

Meanwhile, if the comparison (step 320) reveals that the values are now sufficiently different such that the change (e.g., delta) in vehicle operation data is possibly indicative of bad fuel being present in the vehicle 210, then the telematics device 216 further considers the delta in the pre- and post-refueling readings from the odometer 222 and clock 226. As explained earlier, a refueling event profile record stores the current odometer reading at the time of refueling, as well as the time of refueling.

Figure 4:
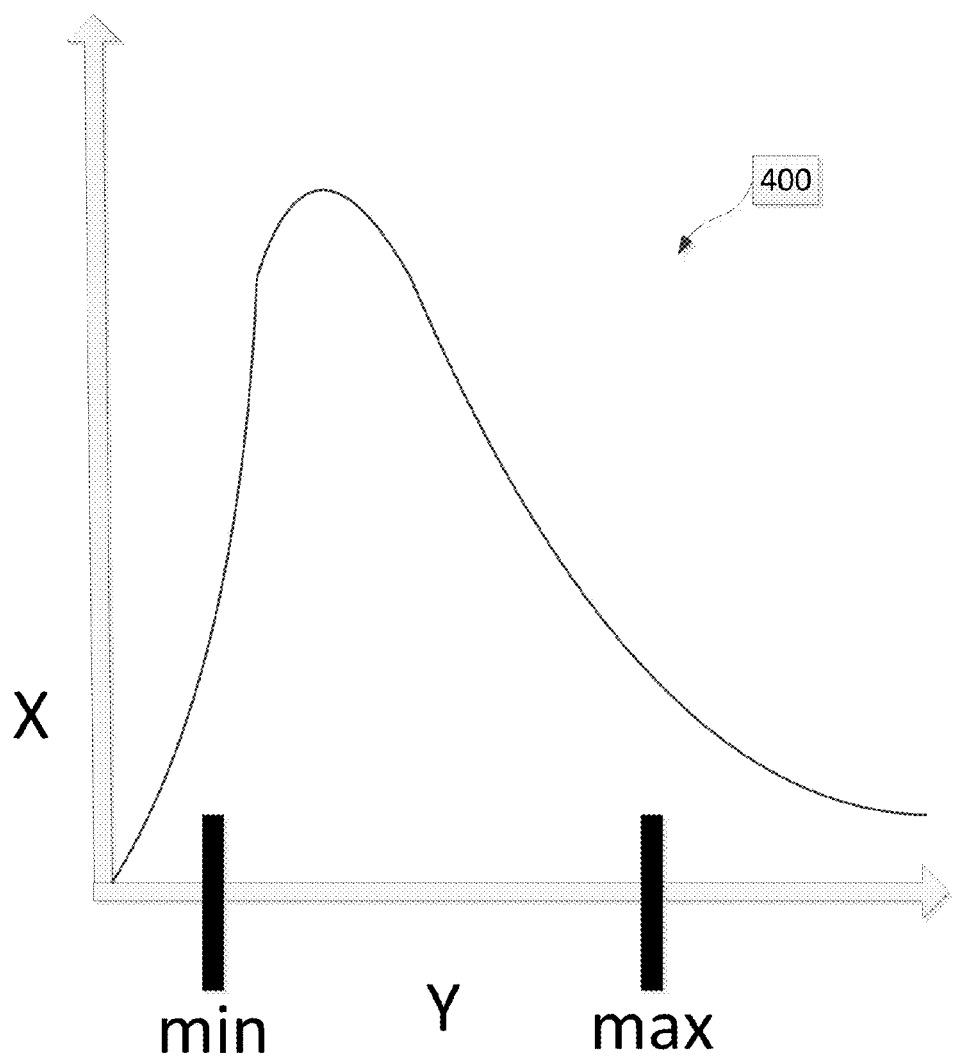
FIG. 4 is a graphical illustration of the confidence level of a bad fuel prediction plotted against the miles driven by a vehicle after refueling, in accordance with one or more aspects of the disclosure.

Therefore, in step 322, the telematics device 216 compares the delta in the odometer reading and/or lapse of time. Based on these values, the delta detected in the vehicle operation data in step 320 may be assigned varying levels of confidence to the telematics device's 216 prediction that bad fuel is present in the vehicle 210. If the delta in distance is below a predetermined minimum threshold value (e.g., one mile, two miles, or other distance), then the telematics device 216 may determine that insufficient miles have been driven with the new fuel to accurately determine whether the new fuel has entered and been used by the vehicle's 210 engine. Meanwhile, if the distance is above a predetermined maximum threshold value, then the telematics device 216 may determine that too many miles have lapsed with the refueled fuel such that it's unlikely that the cause of any anomalies in the vehicle operation data readings is being caused by bad fuel. In other words, a graphical representation of the confidence level of the prediction of bad fuel (along Y-axis of the graph) to the miles driven (along X-axis of the graph) would be a modified bell curve as depicted in FIG. 4. In another example, the relationship between the amount of fuel consumed plotted against the amount of fuel just added may be considered in determining the confidence level of the prediction of bad fuel.

While the curve in FIG. 4 considers the number of miles driven since a refueling event, the telematics device 216 may in some examples further consider the amount of time that has lapsed since the refueling event when determining the confidence in its prediction of bad fuel. This consideration of elapsed time since refueling exemplifies the "garage" example. If the "garage" example, the large passage of time (i.e., two days) since the refueling event lowers the confidence in the bad fuel prediction because it creates numerous possibilities for an intervening event or act since the refueling event to be the cause of vehicle anomalies. For example, someone could have tampered with the fuel tank's contents while the vehicle 210 was parked for the two days. As such, with all things being equal, when the time value is large, the telematics device's 216 confidence level in its prediction of bad fuel is lowered.

Furthermore, in some examples, the telematics device 216 may be further enhanced to consider other values in the refueling event profile record. For example, the telematics device 216 may adjust its confidence level based on whether the refuel event profile indicates that a nearly empty fuel tank was being filled, or whether the refuel event resulted in a ¾-full tank being filled full. In the scenario of the empty fuel tank being filled, the telematics device 216 may adjust higher its confidence level in the bad fuel prediction because the fuel being added is nearly all new fuel from the refueling source at the time of the refueling event. In yet another example, the extent to which the delta in the vehicle operation data negatively adjusts with each subsequent measurement cycle may also be indicative of the confidence level that bad fuel is the cause of the vehicle anomalies. In addition, some types (e.g., characteristics) of vehicle operation data may be assigned more weight than other types in their ability to predict bad fuel. Other examples of factors that are considered and data from the refueling event profile record that may be used to adjust the confidence level of a bad fuel prediction will be apparent to a person of skill in the art after review of the entirety disclosed herein.

Referring to FIG. 3C, after the telematics device 216 determines that a statistically significant delta exists in the appropriate vehicle operation data (in step 322), the processor 103 of the telematics device 216 assigns a confidence level/score to the detection of a possible bad fuel event. In some examples, the confidence level may be a numeric value (e.g., a value between 0 and 100, or other ranges) or from an enumerated list (e.g., low, medium, high, or other values), or other designation that shows varying degrees. Based on confidence level, the telematics device 216 performs one of the possible corresponding steps 323, 324, or 325.

For example, if the delta in the vehicle operation data values is indicative of bad fuel, then the fuel analysis system 200 may trigger the appropriate action. Some illustrative examples of the system's appropriate outcome include, but are not limited to: (1) marking the vehicle's 210 refueling event profile already recorded in computer memory with a flag indicating bad fuel; (2) marking the vehicle's 210 refueling event profile already recorded in computer memory with a flag indicating a medium confidence of bad fuel; (3) marking the vehicle's 210 refueling event profile already recorded in computer memory with a flag indicating a low confidence of bad fuel; and/or (4) for the vehicle's 210 refueling event profile already recorded in computer memory, clearing (e.g., setting to "0") any flag indicating bad fuel. In an illustrative example where the fuel analysis system 200 marks the vehicle's 210 refueling event profile with a flag indicating bad fuel, the outcome is that the telematics device 216 generates an alert to inform the user (e.g., driver, owner, insurance policy holder, or other person with an interest in the good operation of the vehicle) that the vehicle 210 contains bad fuel.

In step 323, any delta values and other factors (e.g., distance traveled since the refueling event, time elapsed since refueling event, and/or other factors) may be analyzed to assign a "low" confidence score to the bad fuel prediction. Meanwhile, in step 324, the delta values and other factors are analyzed to determine that the bad fuel prediction has only a "medium" confidence score. Finally, in step 325, the delta values and other factors are analyzed to determine that the bad fuel prediction has a "high" confidence score. A skilled person after review of the entirety disclosed herein will appreciate that the confidence level outcomes need not be limited to just three, but may be more or less than three as desired.

As a result of the high confidence level in step 325, the telematics device 216 in step 326 may generate an alert to the user (e.g., driver, owner, policyholder, etc.) of the vehicle 210 to indicate that bad fuel has been detected. In one example, the generated alert may be in the form of a visually perceptible display on the dashboard of the vehicle 210. In other examples the generated alert may be output in an audible manner, visual manner, and/or combination thereof. Other illustrative alerts are described herein and are contemplated.

In instances where the prediction of a telematics device 216 results in a "medium" confidence level in step 324, then the telematics device 216 might not generate an alert to the user. Rather, the telematics device 216 may continue to monitor the vehicle operation data of the vehicle 210 to further refine its prediction. For example, the delta in the relevant vehicle operation data may widen/increase with subsequent measurements, thus strongly suggesting that bad fuel in the vehicle 210 is the culprit. In such examples, when step 320 is subsequently re-performed, the telematics device 210 may later take the path of step 325 to a high confidence level.

Finally, in some examples the prediction of the telematics device 216 may result in a "low" confidence level in step 323. Then the telematics device 216 might not generate an alert to the user even though step 322 determined that bad fuel might be present in the vehicle 210. The low confidence level in the measurement by the enhanced bad fuel sensor system 200 may cause the telematics device 216 to continue to monitor the vehicle operation data of the vehicle 210 to further refine its prediction. For example, the delta in the relevant vehicle operation data may widen/increase with subsequent measurements, thus more persuasively suggesting that bad fuel in the vehicle 210 is the culprit. In such examples, when step 320 is subsequently re-performed, the telematics device 210 may later take the path of step 324 to a medium confidence level and then eventually a high confidence level.

In an optional vehicle 210 where a native bad fuel sensor may be present, the output from steps 323, 324, 325 may be used to confirm the accuracy or inoperability of the bad fuel sensor. If the enhanced bad fuel sensor system 200 does not detect bad fuel in step 320, but the native bad fuel sensor does detect bad fuel, this may be an indication that the native bad fuel sensor is malfunctioning. An appropriate alert or message may be displayed to the user, such as through the triggering of a diagnostic troubleshooting code (DTC) through the on-board diagnostics (e.g., OBDII) interface of the vehicle 210 (or through another troubleshooting interface).

While the "garage" example in FIG. 3C illustrates the technological improvements disclosed with respect to more accurately detecting bad fuel through the synergy achieved by coupling the readings from multiple sensors and components, such as odometer, clock/timer, vehicle sensors, and others, the "garage example" also illustrates that rather than simply considering absolute sensor readings, the enhance bad fuel sensor system 200 may compare the change in sensor readings from before and after an event (e.g., a refueling event) to more accurately detect bad fuel after a refueling. These features also provide a significant technological improvement in the art. However, the disclosure contemplates further improving the accuracy of bad fuel detection by implementing crowdsourcing functionality, as described below.

By way of overview, in yet another example (i.e., "crowdsourcing" example), an enhanced bad fuel sensor system 200 may query a fuel analysis server 220 to enhance the accuracy of a determination that a bad fuel measurement is not generating a false positive. In the example of FIG. 3B, the accuracy of the input factors (e.g., a delta in the values of those vehicle operation data variables that are indicative of bad fuel, a delta in vehicle odometer 222 readings, a delta in clock 226 readings, etc.) described above with respect to FIG. 3A may be enhanced with an additional input factor: information from crowdsourcing functionality. The disclosure contemplates other examples of uses of the system 200 disclosed herein and should not be construed to be limited to just the examples expressly described herein.

In FIG. 3B, the enhanced bad sensor system 200 may incorporate wireless communication with a remote server, e.g., fuel analysis server 220, to provide for crowdsourcing functionality. Fundamental to the crowdsourcing functionality is the contribution/aggregation of multiple vehicles 210a-n to the vehicle operation database 227. As explained herein, in step 314, the information transmitted from vehicles 210a-n to a remote server computer machine 225 may be recorded in a vehicle operation database 227 and used for analysis by a fuel analysis module 221.

The fuel analysis module 221 may execute on the same physical server computer as the vehicle operation database 227, or these components of the fuel analysis system 200 may communicate over a network. In addition, a refueling event profile record may be generated at each vehicle 210 and transmitted to the fuel analysis module 221 for analysis. Because the responsiveness of the crowdsourcing functionality in the fuel analysis system 200 is important, the refueling event profile records may be stored in a plurality of database tables to improve the performance of the system 200. In one example, the refueling event profile record are stored at a fuel analysis server 220 comprising the fuel analysis module 221. The plurality of tables may be organized such that a first table stores all refueling event profile records with a similar location measurement, and a second table stores all refueling event profile records that correspond to a different location measurement. In other words, if a first vehicle 210a refuels at a gas station located at the physical street address, 10 South Wacker Drive, then the corresponding refueling event profile record generated at the time of the refueling event is stored in the first table. Nevertheless, if a second vehicle 210b refuels at the same gas station as the first vehicle, the location measurement determined by the sensors of the second vehicle 210b might not be identical to those of the first vehicle 210a because a gas station occupies a multitude of GPS coordinates. As such, the fuel analysis module 221 may accommodate for the discrepancy in exact location measurements by grouping all similar location measurements into the same table. In some examples, the fuel analysis module 221 may be provided with a set of coordinates that map out the perimeter of a particular refueling location. In other examples, the fuel analysis module 221 may identify whichever predefined refueling location is in the closest proximity to the location measurement of the vehicle 210.

As a result, the plurality of refueling event profile records are stored/organized in a plurality of database tables 500 such that, in one illustrative example of FIG. 5, the fuel analysis module 221 executes, with a single search query, the step of updating the confidence score provided by the telematics device 216 (in step 322) into a more accurate, updated confidence score. The single search query is possible because the fuel analysis module 221 optimizes the storage of the data such that the data that would most improve the probability of predicting bad fuel from the fuel provider site is collected into a single searchable table. An example of a single search query in accordance with the preceding example is a search parameter including the location field/column of the table. The results returned from the search query may be limited to just those refueling event profile records with a time field/column that is within, for example, one day before and/after the date/time provided by the vehicle 210 the subject of the search. In other example, a larger or smaller time window may be used to limit the amount of data returned by the search query.

Continuing with the preceding example illustrated in FIG. 5, the data returned from the search query is analyzed by the fuel analysis module 221 to further improve the accuracy of the physical sensor measurements captured at the user vehicle 210. While prior art vehicle systems already included the sensors used in the system 200 described herein, the prior art systems failed to couple the readings from multiple sensors and consider their aggregation (e.g., crowdsourcing feature) to more accurately identify bad fuel in a vehicle's 210 fuel tank. The aspects of the fuel analysis module 221 illustrated in FIG. 5, show that, in one example, data about the operation of other vehicles 210a-n that also refueled from the same location at relatively similar times helps to improve the logical sensor system's ability to predict and identify bad fuel. In another example, a group score may be calculated and used to provide a shared confidence score for the group of vehicles and/or users. The group may be segmented based on those vehicles 210a-n that also refueled from the same location at relatively similar times. As such, the calculated group score may correspond to the quality of fuel provided by the refueling station located at that location. Alternatively, the group score may be used for other purposes or objectives.

The timing of the refuel event provides valuable insight into whether the particular batch of fuel being provided to vehicles contained contaminants or otherwise caused vehicles to malfunction. Absent the system 200 being provided with information about when a particular fueling station (or for that matter, at a more granular level, what particular pump at a fueling station) has been replenished with a new batch of fuel from an oil-transport tanker, the fuel analysis module 221 may assess the probability that the same batch of fuel is being provided to vehicles based on the time of refueling. In one example, if the two immediately preceding records in the database table are within one day of the current vehicle's refueling event, and both of those two immediately preceding records indicate a high confidence of bad fuel, then the current vehicle's confidence score may be elevated from its current score to the next highest confidence score. In other words, if the vehicle 210 detected, in step 320, a difference in pre- and post-refueling vehicle operation data, then whatever confidence score the telematics device 216 calculated, in step 322, is increased due to this crowdsourcing feature. Similarly, if both immediately preceding records indicate no bad fuel, but the vehicle 210 still detects, in step 320, a difference in pre- and post-refueling vehicle operation data, then the confidence score calculated, in step 322, is decreased due to the crowdsourcing feature.

Continuing with the preceding illustration, assume that in this example the vehicle 210 was poorly maintained by its owner. Because of this, numerous of the vehicle operation data measured by its vehicle sensors 212 were already outside an ideal range of operation before the time of its refueling event. With prior art vehicle sensors that measure vehicle operation data in isolation, the measurements would be insufficient to accurately identify bad fuel, or worse, they might identify a false positive. With the novel and non-obvious technical system 200 disclosed herein, the pre- and post-refueling values of the vehicle operation data are compared, in step 320, to determine if the vehicle operates even worse after the refueling event. Even if readings show that the vehicle operates worse after refueling, in step 322, the confidence score assigned to the bad fuel determination is low. This is because, in some examples in step 322, an additional factor considered in determining the confidence score to assign the probability of actual bad fuel in the vehicle is the overall condition of the vehicle 210 before refueling. A vehicle that has numerous operational defects prior to refueling is a less confident representative (e.g., leading indicator) to predict bad fuel. Rather, in this example, a low confidence score (e.g., only 20 out of 100 points) may be assigned to the confidence score field of the refueling event profile record of the vehicle 210.

In spite of the low confidence score, the fuel analysis system 200 described herein is a further enhancement over the measurement of isolated sensors in a vehicle because the system 200 provides, in some examples, a crowdsourcing feature. Continuing with the preceding example, assume the poorly maintained vehicle 210 received bad fuel when it refueled at time t1=100. Although a telematics device 216 of the vehicle 210 performs the steps of FIG. 3C and follows the "low confidence" path towards step 323, the fuel analysis module 221 may further enhance the telematics device's 216 determination. Specifically, the fuel analysis module 221 may consider the database table 500 in FIG. 5. In searching the table 500, assume the fuel analysis module 221 finds that a dozen other vehicles 210a-n with records in that same table (i.e., that share similar location measurements because they were refueled at the same gas station) have detected bad fuel with a high confidence score. Also assume the timestamp on the refueling event profile record of those vehicles is within a window of time 30 minutes before and/or after that of the subject vehicle 210 having refueled. This statistically significant detection of numerous occurrences of bad fuel in close time proximity to the subject vehicle 210 elevates the confidence score of the subject vehicle 210. In this example, assume the subject vehicle 210 is, like the vehicle in the "garage" example of FIG. 3C, parked in a garage immediately after having refueled. In such a case, the telematics device 216 may pre-emptively receive an alert from the fuel analysis server 220 stating that the user of the vehicle 210 should take precautions against the bad fuel in the vehicle's gas tank. In stark contrast to prior art vehicles with sensors, in the example disclosed herein, the vehicle 210 need not incur irreparable damage and anomalous vehicle operation data before affirmatively identifying bad fuel in the vehicle. In addition to being a technological innovation in the art, the system 200 disclosed herein potentially saves drivers, vehicle owners, insurance companies, and other parties a significant expense in both time and money.

The previous example highlighted that the fuel analysis module 221 may provide, in some examples, two different bad fuel detection steps: (1) updating the confidence score determined by the telematics device 216 using aggregated data from other vehicles 210a-n, and (2) pre-emptively generating alerts to telematics devices (or their users) to notify them of bad fuel present in their vehicles. Each of these bad fuel detection steps performed by the fuel analysis module 221 are described in relation to the "warning" example in FIG. 3D below.

By way of overview, in another example (i.e., "warning" example), a fuel analysis server 220 may generate a notification (e.g., an alert) to pre-emptively alert vehicles 210a-n that they may have been refueled with bad fuel, and others, such as fuel providers, insurance policy providers, roadside assistance service providers, and others. The disclosure contemplates other examples of uses of the fuel analysis system 200 disclosed herein and should not be construed to be limited to just the examples expressly described herein.

Figure 3D:
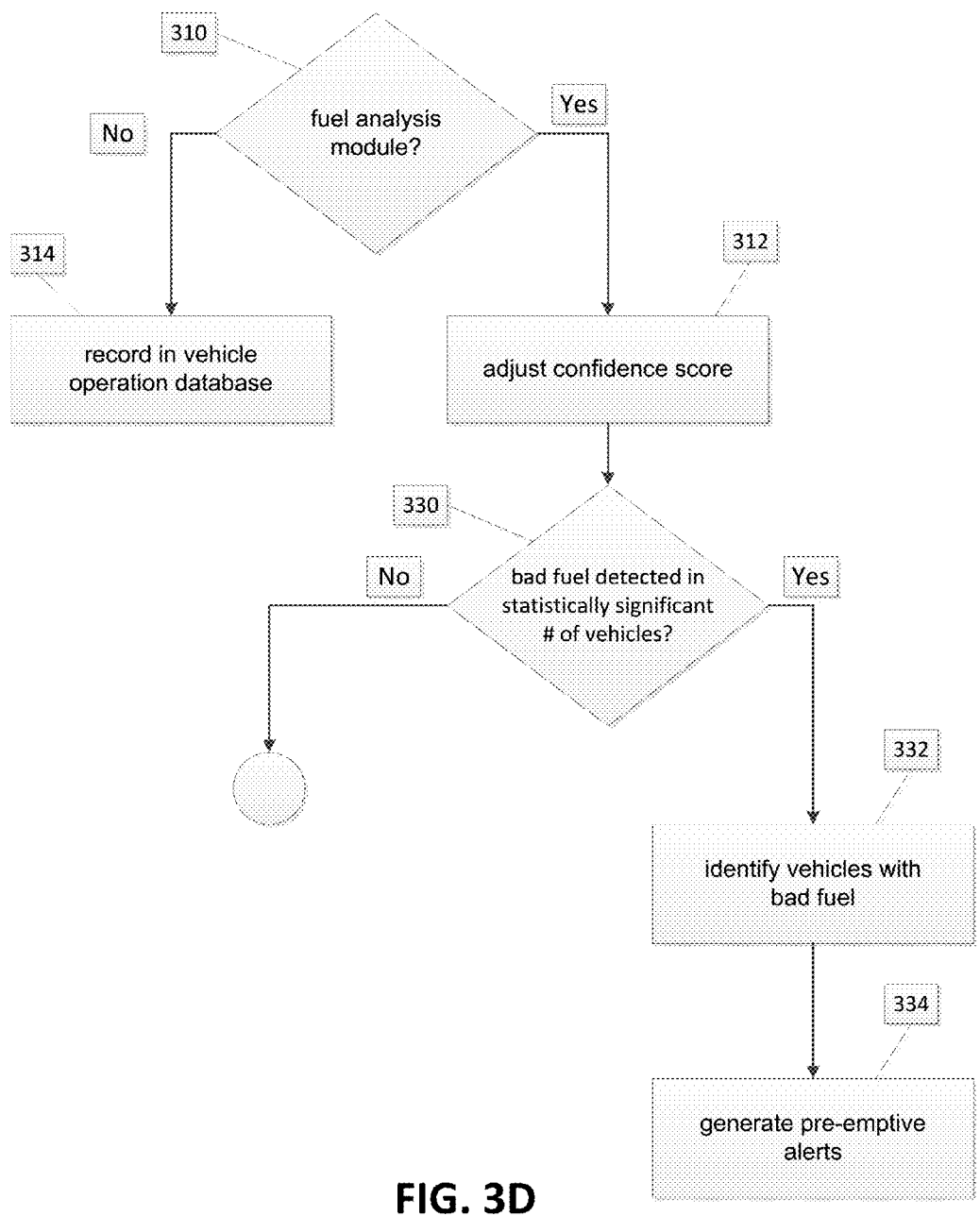

Referring to FIG. 3D, assuming the decision in step 310 leads down the path to step 312 in which the confidence score determined at the telematics device 216 is adjusted based on crowdsourcing information, then the fuel analysis module 221 may further check if any pre-emptive generation of alerts is desired. For example, in adding yet another data point to its table 500 of vehicle refueling event profile information associated with a particular fueling station, the fuel analysis module 221 may, in step 330, check if a statistically significant trend has emerged in the data set. For example, as described in one example above, if a dozen vehicles 210a-n from a single table 500 all had refueling events within a close time proximity of one another, and also have detected bad fuel with a high confidence score, then this statistically significant detection may trigger the system 200 to pre-emptively generate alerts to other vehicle's telematics devices (or their users) to notify them of the high likelihood of bad fuel present in their vehicles. The list of these vehicle telematics devices may be generated in step 332. The list may be based on the time of the refuel event for each of vehicle. For example, assume a first, second, and third vehicle that refueled (in that order) from a specific gas station have identified bad fuel with a high confidence; and likewise, a sixth, seventh, and eighth vehicle that refueled (in that order) at the same specific gas station also have identified bad fuel with a high confidence. Then, there is a high probability that the fourth and fifth vehicles, which refueled at the same gas station in-between the other affected vehicles, also contain bad fuel. In such an example, the fuel analysis module 221 may cause the fuel analysis server 220 to transmit a notification (see step 334) to the telematics device 261 of the affected vehicle 210 that causes the telematics device 261 to output the alert through its user interface. The alert may take the form of an informative message, a warning message, a danger message, or other output, either visual, audible, or otherwise sensory.

The fuel analysis server 220 may also communicate with others, such as fuel providers, insurance policy providers, roadside assistance service providers, and others. In some examples, the fuel analysis server 220 may communicate with the vehicle's insurance company to pre-emptively begin insurance claim processing. This almost pre-first notice of loss (pre-FNOL) approach to processing the insurance claim may save the user (e.g., insurance policyholder) significant time when submitting a new claim for vehicle damage caused by bad fuel. In such examples, the insurance company's server machine (e.g., server 233) may have received the requisite evidence (e.g., vehicle operation data, refueling event profile records) from the fuel analysis server 220 before the policy holder even contacts the insurance company to report a FNOL.

In addition, the fuel analysis server 220 may generate an alert to the fuel provider and/or fuel operator to notify them of the bad fuel. At a minimum, the fuel operator may halt the further sale of the bad gas and test the bad gas for contaminants. While prior art systems existed to test the contaminants in fuel, no existing system made it possible to aggregate the collective sensor system measurements of a plurality of vehicle sensors across multiple vehicles 210a-n. With this new technological advancement in the system, the benefits of the crowdsourcing feature described herein are recognized.

In yet another example, the fuel analysis server 220 may generate an alert to a roadside assistance service provider to notify them of the bad fuel. The roadside assistance service providers may accordingly prepare and dispatch tow trucks and supplies/equipment into the field in preparation for likely service calls. The end result is a faster response time for drivers stranded along the roadside in their vehicles filled with bad fuel.

Building upon the examples described herein, the disclosure contemplates the creation of a new factor/input for consideration in the underwriting and administration of vehicle insurance policies and insurance claims. For example, the repeated occurrence of bad fuel in a user's vehicle 210 may indicate an elevated level of risk associated with the vehicle. As a result, the vehicle 210 may be a higher risk to insure. In addition, the results from the fuel analysis system 200 may be stored in an insurance policy database 238 in the fuel analysis server 220 such that the information may be retrieved by an external server 233 for purposes of calculating insurance premiums and policy parameters.

In addition, in user vehicles 210 equipped technology systems to track driving behavior (e.g., hard braking, cornering, speeding, etc.), the fuel analysis system 200 may interact with the driving behavior tracking system to disregard that telematics data collected while bad fuel was in the vehicle 210. In particular, the interaction between the systems results in any driving score calculated for the vehicle 210 and/or user of the vehicle 210 to be adjusted to accommodate for the bad fuel such that the user/vehicle is not unfairly penalized for anomalies in driving behavior due to the bad fuel.

In addition, the data collected by the fuel analysis system 200 may be packaged into a verified report and automatically submitted with an insurance claim. For example, where the bad fuel results in damage to the vehicle and/or other property/life, the packaged report may serve as evidence in a trial to determine the proximate cause of any damage. Given that the collected data may be entered for use in a trial, the fuel analysis system 200 may also include mechanisms by which the authenticity of the data is verified.

In addition, some aspects of the disclosure relate to a crowdsourcing feature that may act on its own to assist in claims processing. For example, the total loss value of a vehicle 210 may be adjusted even before a policyholder has submitted a claim because the crowdsourcing feature may identify the location of the vehicle and determine that numerous other vehicles at a similar location at a similar time also have filed for the same claim. The insurance company may aggregate this information, and pre-emptively contact the policyholder with a pre-populated claims submission form and claims check authorization. Moreover, in some examples, the total loss value of the vehicle 210 may be adjusted based on the damage likely sustained to the vehicle during the loss event. The loss event might be a hurricane, tornado, flood, other nature-made event, or man-made event (e.g., bombing, explosion, etc.). For example, a barometer sensor in a vehicle 210 may sense a barometric pressure change as a result of a hurricane or tornado event. Other vehicles in the same area at the same time as the vehicle 210 may or may not have barometer sensors, nevertheless, through the crowdsourcing feature of the system 200, the cause of their anomalous vehicle operation is tracked back to the appropriate event. In summary, any event that likely may have been shared with a plurality of vehicles 210a-n that were located in a similar place at a similar time may be detected, analyzed, and acted upon by the crowdsourcing feature of the contemplated system 200 described herein.

A person of skill in the art, after reading the entirety disclosed herein, will recognize that various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space). While the aspects described herein have been discussed with respect to specific examples including various modes of carrying out aspects of the disclosure, those skilled in the art will appreciate that there are numerous variations and permutations of the above described systems and techniques that fall within the spirit and scope of the invention. In addition, while the elements 225, 220 are shown in FIG. 2A are depicted as separate blocks, any or all of these elements may be physically and/or logically combined together and/or further physically and/or logically subdivided as desired.

The invention claimed is:

1. An enhanced sensor system to detect bad fuel in a user vehicle, the system comprising:
   the user vehicle equipped with sensors configured to repeatedly measure a plurality of vehicle operation data indicative of bad fuel, wherein the sensors comprise an odometer, a clock, and a fuel level gauge, and wherein the repeated measuring occurs at least at a pre-refueling time that is before a refueling event and at a post-refueling time that is after the refueling event;
   a telematics device coupled to the user vehicle, the telematics device comprising an electronic interface to the sensors of the user vehicle, a wireless communication circuitry, a user interface configured to communicate an alert to a user of the user vehicle, a processor configured to calculate a probability of having received bad fuel at the refueling event, and a computer memory; and
   a server machine in wireless, remote communication with the wireless communication circuitry of the telematics device, the server machine comprising:
     a vehicle operation database configured to store the plurality of vehicle operation data measured by the sensors, and
     a fuel analysis module, which is communicatively coupled to the vehicle operation database, configured to improve an accuracy of the probability of bad fuel calculated by the processor of the telematics device;
   wherein the telematics device detects the refueling event upon receiving a substantial increase in a measurement of the fuel level gauge of the user vehicle;
   wherein the telematics device receives, through the electronic interface of the telematics device, the vehicle operation data measured by the sensors of the user vehicle at the pre-refueling time and at the post-refueling time;
   wherein the computer memory of the telematics device comprises a non-volatile memory configured to store a refueling event profile record after detecting the refueling event, wherein the refueling event profile record comprises:
     a last set of the plurality of vehicle operation data repeatedly measured by the sensors of the user vehicle before the refueling event;
     the measurement of the fuel level gauge upon completion of the refueling event;
     a distance measurement, by the odometer, at the refueling event;
     a time measurement, by the clock, at the refueling event; and
     a location measurement, by a global positioning satellite (GPS) unit, at the time of the refueling event;
   wherein the processor of the telematics device is configured to:
     compare the vehicle operation data of the refueling event profile with vehicle operation data at the post-refueling time;
     determine that the two sets of vehicle operation data are different such that the probability of having received bad fuel at the refueling event is greater than zero;
     calculate a first confidence score for the probability of bad fuel based on a delta in the distance measurements and a delta in the time measurements during the comparing step; and
     send, through the wireless communication circuitry, the first confidence score to the server machine;
   wherein the fuel analysis module of the server machine is configured to:
     receive the first confidence score;
     update the first confidence score into a second confidence score based on those confidence scores provided by other vehicles associated with refueling event profile records that store a similar location measurement and similar time measurement as the refueling event profile record of the user vehicle; and
     send the second confidence score to the telematics device; and
   wherein, upon receipt of the second confidence score at the telematics device, the user interface of the telematics device is configured to communicate the alert to the user of the user vehicle, wherein the alert indicates that the user vehicle was filled with bad fuel at the refueling event.

2. The system of claim 1, wherein the calculating the first confidence score for the probability of bad fuel includes:
   decreasing the first confidence score when the last set of vehicle operation data stored in the refueling event profile record indicate negative values;
   increasing the first confidence score when the delta in the time measurement is below a threshold time value;
   decreasing the first confidence score when the delta in time measurement is above a maximum value and the delta in the distance measurement is below the minimum threshold distance value;
   increasing the first confidence score when the delta in the distance measurement is above a minimum threshold distance value;
   increasing the first confidence score when the last set of vehicle operation data stored in the refueling event profile record indicates that the fuel level gauge was below a threshold fuel level value and the measurement of the fuel level gauge upon completion of the refueling event indicates at least a twenty five percent increase in fuel level gauge; and
   increasing the first confidence score when a delta in particular vehicle operation data indicative of bad fuel negatively increase with repeated measurements by the sensors.

3. The system of claim 1, wherein the second confidence score is higher than the first confidence score when a second vehicle, which refueled at the similar location and at the similar time as the user vehicle, calculated with a high confidence score that the second vehicle received bad fuel at its refueling event.

4. The system of claim 3, wherein the fuel analysis module comprises a plurality of database tables;
wherein a first table of the plurality of database tables comprises all refueling event profile records with the similar location measurement, and a second table of the plurality of tables comprises all refueling event profile records with a location measurement similar to a second location; and
wherein the plurality of database tables are organized such that the fuel analysis module executes the step of updating the first confidence score to the second confidence score with a single search query.

5. The system of claim 1, wherein the plurality of vehicle operation data indicative of bad fuel comprises at least one of measurements from: an engine revolutions per minute (RPM) sensor, a rate of fuel consumption sensor, an oxygen sensor, and an engine stalling sensor.

6. The system of claim 1, wherein the electronic interface to the sensors of the user vehicle is an on-board diagnostics (OBD) port.

7. The system of claim 1, wherein the user vehicle comprises the GPS unit.

8. The system of claim 7, wherein the telematics device comprises the GPS unit.

9. The system of claim 7, wherein the user vehicle is an electric vehicle comprising an engine at least partially powered by an electric battery, wherein the fuel level gauge is configured to measure electric charge remaining in the electric battery, and wherein the substantial increase in the fuel level gauge amounts to more than a predetermined threshold increase in the electric battery's charge.

10. The system of claim 1, further comprising:
a roadside server provider vehicle equipped with electronic circuitry to receive the alert from the server machine identifying the user vehicle as a victim of bad fuel,
wherein the alert comprises information about the vehicle operation data of the user vehicle.

11. The system of claim 1, further comprising:
an insurance server, in remote communication with the server machine, configured to receive the alert indicating bad fuel in the user vehicle,
wherein the insurance server pre-emptively initiates first notice of loss (FNOL) insurance claim processing for a possible claim submitted for the user vehicle with bad fuel.

12. A bad fuel detection system comprising:
a telematics device coupled to a user vehicle, the telematics device comprising an electronic interface to sensors of the user vehicle, a wireless communication circuitry, a user interface configured to communicate an alert to a user of the user vehicle, a processor configured to calculate a probability of having received bad fuel at a refueling event, and a computer memory; and
a server machine in wireless, remote communication with the wireless communication circuitry of the telematics device, the server machine comprising:
a vehicle operation database configured to store a plurality of vehicle operation data indicative of bad fuel measured by the sensors, and
a fuel analysis module, which is communicatively coupled to the vehicle operation database, configured to improve an accuracy of the probability of bad fuel calculated by the processor of the telematics device;
wherein the processor of the telematics device is programmed to perform steps comprising:
detecting a refueling event upon receiving a substantial increase in a measurement of a fuel level gauge sensor of the user vehicle;
receiving, through the electronic interface of the telematics device, the vehicle operation data measured by the sensors of the user vehicle at a pre-refueling time that is before the refueling event and at a post-refueling time that is after the refueling event;
after detecting the refueling event, storing, in the computer memory of the telematics device, a refueling event profile record comprising:
a last set of the vehicle operation data measured by the sensors before the refueling event;
a measurement of the fuel level gauge upon completion of the refueling event;
a distance measurement, by an odometer sensor of the user vehicle, at the refueling event;
a time measurement, by a clock of the user vehicle, at the refueling event; and
a location measurement, by a global positioning satellite (GPS) unit, at the time of the refueling event;
comparing the vehicle operation data of the refueling event profile with vehicle operation data measured at the post-refueling time;
determining that the two sets of vehicle operation data are different such that the probability of having received bad fuel at the refueling event is greater than zero;
calculating a first confidence score for the probability of bad fuel based on a delta in the distance measurements and a delta in the time measurements during the comparing step;
sending, through the wireless communication circuitry, the first confidence score to the server machine; and
upon receipt of an updated first confidence score at the telematics device, causing the user interface of the telematics device to communicate an alert to the user of the user vehicle, wherein the alert indicates that the user vehicle was filled with bad fuel at the refueling event.

13. The system of claim 12, wherein the fuel analysis module is programmed to perform steps comprising:
receiving the first confidence score;
updating the first confidence score based on those confidence scores provided by other vehicles associated with refueling event profile records that store a similar location measurement and similar time measurement as the refueling event profile record of the user vehicle; and
sending the updated first confidence score to the telematics device.

14. The system of claim 12, wherein the calculating the first confidence score for the probability of bad fuel includes at least one of:
increasing the first confidence score when the delta in the time measurement is below a threshold time value;
decreasing the first confidence score when the delta in time measurement is above a maximum value and the delta in the distance measurement is below the minimum threshold distance value; and
increasing the first confidence score when the delta in the distance measurement is above a minimum threshold distance value.

15. The system of claim 12, wherein the calculating the first confidence score for the probability of bad fuel includes at least one of:
- decreasing the first confidence score when the last set of vehicle operation data stored in the refueling event profile record indicate negative values;
- increasing the first confidence score when the last set of vehicle operation data stored in the refueling event profile record indicates that the fuel level gauge was below a threshold fuel level value and the measurement of the fuel level gauge upon completion of the refueling event indicates at least a twenty five percent increase in fuel level gauge; and
- increasing the first confidence score when a delta in particular vehicle operation data indicative of bad fuel negatively increase with repeated measurements by the sensors.

16. The system of claim 12, wherein the plurality of vehicle operation data indicative of bad fuel comprises at least one of measurements from: an engine revolutions per minute (RPM) sensor, a rate of fuel consumption sensor, an oxygen sensor, and an engine stalling sensor, and wherein the telematics device comprises the GPS unit.

17. A method comprising:
- detecting, by a processor of a telematics device coupled to a user vehicle, a refueling event upon receiving a substantial increase in a measurement of a fuel level gauge sensor of the user vehicle;
- receiving, through an electronic interface of the telematics device, vehicle operation data measured by sensors of the user vehicle at a pre-refueling time that is before the refueling event and at a post-refueling time that is after the refueling event;
- after detecting the refueling event, storing, in a computer memory of the telematics device, a refueling event profile record comprising:
  - a last set of the vehicle operation data measured by the sensors before the refueling event;
  - a measurement of the fuel level gauge sensor upon completion of the refueling event;
  - a distance measurement, by an odometer sensor of the user vehicle, at the refueling event; a time measurement, by a clock of the user vehicle, at the refueling event; and
  - a location measurement, by a global positioning satellite (GPS) unit, at the time of the refueling event;
- comparing, by the processor, the vehicle operation data of the refueling event profile record with vehicle operation data measured at the post-refueling time;
- determining, by the processor, that the two sets of vehicle operation data are different such that a probability of having received bad fuel at the refueling event is greater than zero;
- calculating a confidence score for the probability of bad fuel based on a delta in the distance measurements and a delta in the time measurements during the comparing step;
- sending, through a wireless communication circuitry of the telematics device, the confidence score to a server machine remotely located to the user vehicle; and
- upon receipt of an updated confidence score at the telematics device, causing a user interface of the telematics device to communicate an alert to a user of the user vehicle, wherein the alert indicates that the user vehicle was filled with bad fuel at the refueling event.

18. The method of claim 17, wherein the calculating the confidence score for the probability of bad fuel includes at least one of:
- decreasing the confidence score when the last set of vehicle operation data stored in the refueling event profile record indicate negative values;
- increasing the confidence score when the delta in the time measurement is below a threshold time value;
- decreasing the confidence score when the delta in time measurement is above a maximum value and the delta in the distance measurement is below the minimum threshold distance value;
- increasing the confidence score when the delta in the distance measurement is above a minimum threshold distance value;
- increasing the confidence score when the last set of vehicle operation data stored in the refueling event profile record indicates that the fuel level gauge was below a threshold fuel level value and the measurement of the fuel level gauge upon completion of the refueling event indicates at least above a minimum threshold increase in fuel level gauge; and
- increasing the confidence score when a delta in particular vehicle operation data indicative of bad fuel negatively increase with repeated measurements by the sensors.

19. The method of claim 17, wherein the server machine comprises a fuel analysis module that is programmed to perform steps comprising:
- receiving the confidence score;
- updating the confidence score based on those confidence scores provided by other vehicles associated with refueling event profile records that store a similar location measurement and similar time measurement as the refueling event profile record of the user vehicle; and
- sending the updated confidence score to the telematics device.

20. The method of claim 17, wherein the vehicle operation data indicative of bad fuel comprises at least one of measurements from: an engine revolutions per minute (RPM) sensor, a rate of fuel consumption sensor, an oxygen sensor, and an engine stalling sensor.

* * * * *